United States Patent [19]
Fergason et al.

[11] Patent Number: 5,751,258
[45] Date of Patent: May 12, 1998

[54] LIQUID CRYSTAL LENS DRIVER ELECTRONICS FOR EYE PROTECTION, HIGH SPEED SHUTTERING WITH CONSISTENT PERFORMANCE

[75] Inventors: Jeffrey K. Fergason, Menlo Park; John D. Fergason, Mountainview, both of Calif.

[73] Assignee: OSD Envizion, Inc., St. Louis, Mo.

[21] Appl. No.: 707,269

[22] Filed: Sep. 4, 1996

Related U.S. Application Data

[63] Continuation of Ser. No. 27,235, Feb. 17, 1993, abandoned, which is a continuation-in-part of Ser. No. 674,850, Mar. 25, 1991, Pat. No. 5,252,817.

[51] Int. Cl.$^6$ ............................ A61F 9/06; G02F 1/133
[52] U.S. Cl. .................... 345/7; 349/14; 349/16; 2/8
[58] Field of Search ...................... 359/84, 85; 250/205, 250/215, 229; 345/87, 89, 94, 7; 349/13, 14, 116; 2/8

[56] References Cited

U.S. PATENT DOCUMENTS

| | | |
|---|---|---|
| Re. 29,684 | 6/1978 | Gordon . |
| 2,761,046 | 8/1956 | Herrick et al. . |
| 3,245,315 | 4/1966 | Marks et al. . |
| 3,575,491 | 4/1971 | Heilmeier . |
| 3,873,804 | 3/1975 | Gordon . |
| 3,881,808 | 5/1975 | Gurtler et al. . |
| 3,890,628 | 6/1975 | Gurtler . |
| 4,093,832 | 6/1978 | Isaacson et al. . |
| 4,109,114 | 8/1978 | Baer et al. . |
| 4,143,264 | 3/1979 | Gilbert et al. . |
| 4,155,122 | 5/1979 | Budmiger . |
| 4,237,557 | 12/1980 | Gordon ........................ 359/85 |
| 4,240,709 | 12/1980 | Hörnell . |
| 4,279,474 | 7/1981 | Belgorod . |
| 4,328,493 | 5/1982 | Shanks et al. . |
| 4,560,239 | 12/1985 | Katz . |
| 4,664,479 | 5/1987 | Hiroshi . |
| 4,710,694 | 12/1987 | Sutphin et al. . |
| 4,728,173 | 3/1988 | Toth . |
| 4,759,608 | 7/1988 | Yang . |
| 4,821,292 | 4/1989 | Childress . |
| 4,863,244 | 9/1989 | Fuerthbauer et al. . |
| 5,015,086 | 5/1991 | Okaue et al. . |
| 5,074,647 | 12/1991 | Fergason et al. . |
| 5,113,270 | 5/1992 | Fergason . |
| 5,184,156 | 2/1993 | Black et al. ........................ 351/158 |
| 5,208,688 | 5/1993 | Fergason et al. . |

FOREIGN PATENT DOCUMENTS

| | | |
|---|---|---|
| 35615 | 5/1973 | Australia . |
| 0157744 | 9/1985 | European Pat. Off. . |
| 0335056 | 4/1989 | European Pat. Off. . |
| 2530039 | 2/1984 | France . |
| 2315308 | 10/1973 | Germany . |
| 2742211 | 3/1979 | Germany . |
| 3503958 | 8/1986 | Germany . |
| 3842824 | 6/1990 | Germany . |
| 55-92276 | 12/1980 | Japan . |
| 7312733 | 7/1977 | Sweden . |
| 7608690 | 2/1979 | Sweden . |
| 325586 | 2/1930 | United Kingdom . |
| 8805926 | 8/1988 | WIPO . |
| 9014611 | 11/1990 | WIPO . |

OTHER PUBLICATIONS

H686, United States Statutory Invention Registration to Mullins.

*Primary Examiner*—Jeffery Brier
*Attorney, Agent, or Firm*—Howell & Haferkamp, LC

[57] ABSTRACT

A power supply circuit for a liquid crystal welding lens or shutter provides a consistent and stable regulated power signal for driving or powering the liquid crystal shutter for maintaining stable performance over the life of the power supply and a battery level indicator feature to provide advance warning of degraded device performance.

31 Claims, 5 Drawing Sheets

LIQUID CRYSTAL LENS DRIVER ELECTRONICS FOR EYE PROTECTION, HIGH SPEED SHUTTERING WITH CONSISTENT PERFORMANCE

This application is a continuation of application Ser. No. 08/027,235 filed on Feb. 17, 1993 now abandoned which is a continuation-in-part of U.S. patent application Ser. No. 07/674,850 filed on Mar. 25, 1991 now U.S. Pat. No. 5,252,817.

This is a continuation-in-part of copending, commonly assigned U.S. patent application Ser. No. 07/674,850, filed Mar. 25, 1991, the entire disclosure of which hereby is incorporated by reference.

TECHNICAL FIELD

The present invention relates generally, as is indicated, to driving circuits for liquid crystal shutters and, more particularly, to a high speed driving circuit for a liquid crystal shutter operable to control transmission of light therethrough.

BACKGROUND

The present invention is described below with respect to a liquid crystal shutter. It will be appreciated, though, that features of the invention may be utilized with shutters formed of materials other than liquid crystal and also may be utilized with devices other than shutters. A shutter, as is used herein, refers to a device for controlling intensity of electromagnetic energy or electromagnetic radiation that is being transmitted through the shutter. In the preferred embodiment described in detail below, such electromagnetic energy is in the form of light and more preferably is in the form of light (i.e., electromagnetic energy) that is in the visible spectrum as well as in the various infrared spectra and ultraviolet spectra, all collectively referred to as light below. Such control may be by way of graduated or analog control or intensity of transmitted light preferably without detrimentally affecting the image characteristics of such light. Such control also may be digital, i.e., on, off, and specific intermediate levels of transmission or intensity, etc.

An exemplary liquid crystal shutter with which the driving circuit of the invention may be utilized is disclosed in U.S. Pat. Nos. 4,385,806, 4,436,376, 4,540,243, and Re. 32,521. An example of such shutter includes a pair of linear (plane) polarizers, one being used as an input polarizer and the other as an output analyzer, and a variable liquid crystal optical retarder between the two polarizers. By changing the electric field applied to liquid crystal in the retarder, the plane of polarization (or relationships of the axes of elliptically polarized light) of the light transmitted through the retarder can be changed; and the intensity of light transmitted through the analyzer will be a function of the polarization direction (characteristics) of the light transmitted through the retarder.

A shutter system which may employ such an exemplary liquid crystal shutter is disclosed in copending, commonly owned U.S. patent application Ser. No. 07/653,661 filed Feb. 8, 1991, for "Eye Protection System For Welding Helmets And The Like". The present invention is useful to provide electrical power and to operate such a shutter system.

The disclosures of the above patents and patent application are incorporated in their entireties by this express reference thereto.

One approach to providing for high speed operation, for example, in the microsecond range, as compared to the millisecond range, say on the order of 500 microseconds or faster, and preferably in the range of from several microseconds to several tens of microseconds, for the optical shutters of such patents and patent applications, as well as other similar shutters, is according to surface mode effect. Using surface mode effect that liquid crystal material located near the center of the liquid crystal cell along the optical transmission direction through the cell is maintained or generally stays in a preferred alignment during cell operation. However, the liquid crystal material nearer the respective surfaces of the cell, e.g., closer to the interface between the liquid crystal material and the respective glass plates, has its alignment switched to switch the shutter between clear and dark states as a function of the applied electric field, as is described in detail in the above-mentioned patents and patent application. Due to birefringence characteristics of the liquid crystal material, for example, nematic liquid crystal, changes in the thickness of differently aligned liquid crystal layers varies retardation effect on transmitted polarized light. Absent adequate field voltage the liquid crystal near the surface aligns generally parallel or slightly tilted with respect to the surface, and such surface "layer(s)" of liquid crystal tend to align with the field when the field voltage is adequately large. In one embodiment some means, such as a bias voltage or electric field, a functionally equivalent rms driving method, or some other means or mechanism, is used to obtain the preferred alignment of liquid crystal material near the center of the cell. In an example, application of a larger voltage/electric field compared to the exemplary bias voltage/electric field, effects switching of the alignment of the liquid crystal material nearer the surfaces.

As is well known, the transition speed for a liquid crystal cell, whether of the twisted nematic type, dyed cell type or surface mode type, is asymmetrical; in particular, such a liquid crystal cell operates faster to achieve an operational condition, e.g., alignment of liquid crystal structure or directors, when driven to that condition by an electric field (or an increase in the field magnitude), than it operates when relaxing to a deenergized or reduced energization state, e.g., reduction or elimination of the electric field. Therefore, for maximum speed of operation to the dark state for eye protection, for example, it is desirable in a welding lens environment of a liquid crystal shutter that the liquid crystal shutter be operated with maximum power to achieve the darkest eye protection state. Also, a surface mode liquid crystal cell usually responds to energization significantly faster than twisted nematic liquid crystal cell, and it, therefore, provides for faster operation in accordance with the present invention.

The exemplary shutter may be used in a variety of embodiments and applications. One example is as a lens or shutter for a welding helmet. Therefore, the terms "lens" and "welding lens" are used synonymously with "shutter" and, as used herein means the device through which an image is viewed without necessarily having any focusing or optical refraction characteristics. The lens or shutter is adjustable to control light, i.e., to increase or to decrease the amount of the incident light which is transmitted through the shutter. When welding is not occurring, the shutter may be substantially optically clear or transmissive or at least minimizes its attenuation of light. When welding is occurring, the shutter may be dark or closed to minimize the amount of light transmitted therethrough in order to protect the eyes of the person performing the welding. In both cases, though, the image characteristics of the light remain intact. A photosensitive device may be used to sense the intensity of light impinging in the area of the shutter so as to provide an input to a drive circuit for the shutter in order to control opening and closing thereof. As is described in the above patent application, a third state or condition of the welding lens or shutter may exist, namely a deenergized state or condition. Such third state preferably is darker than the clear state.

The invention is especially useful for eye protection wherein high speed protective shuttering and protective fail state are desired. Exemplary uses are in welding helmets, spectacles, goggles, and the like, as well as safety goggles for nuclear flash protection, for protection from hazards experienced by electric utility workers and for workers at furnace and electrical plant areas and at other places where bright light that could present a risk of injury may occur.

Shade number or shade is the characterization of darkness of a welding lens, for example, (hereinafter sometimes simply referred to as lens); a larger shade number represents a darker, more light blocking (of absorbing) or less optically transmissive lens and a smaller shade number represents a less dark, less light blocking (or absorbing) or more optically transmissive lens. Generally optical transmission means transmission of light and the image or view carried by the light without substantial distortion of the image, e.g., due to scattering. Shade number is a term of art often used in the field of welding and especially welding lenses for eye protection.

Clear state or clear shade means the state of highest operating luminous transmittance (or light transmission) of the lens. This state corresponds to the state having the lowest shade number for the lens.

Dark state or dark shade is the lowest operating luminous transmittance (or light transmission) of the lens. This state corresponds to the state having the highest specified shade number for the lens. The invention is described below in some instances indicating that in the dark state no light is transmitted. While this may be desirable for some applications of the principles of the invention, it will be appreciated that for a welding lens in the dark state there will be some transmission so that the welder can see to do the welding while some light is blocked to provide the desired eye protection from damage, injury or the like by the light emitted during welding.

Shutter response time is the time required for the circuitry associated with the lens to detect a sharp increase in incident light (e.g., due to striking of the welding arc, etc.) and to switch the lens from the clear state to the dark state.

Shutter recovery time is the time required for the circuitry associated with the lens to detect a sharp decrease in light (e.g., due to extinguishing of the welding arc, etc.) and to switch the lens from the dark state to the clear state.

Variable transmittance is the ability of the lens to be switched from one level of luminous transmittance (also referred to as transmission of light) to another level of luminous transmittance in response to a change in incident illumination.

Dynamic operational range or dynamic optical range of the welding lens or shutter is the operational range of the lens between the dark state and the clear state, e.g., the difference between the shade numbers of the dark state and the clear state.

When the shutter is used for eye protection where high speed shuttering is desirable to protect the vision of the user, it is further desirable that the device is small and portable relying on batteries or rechargeable capacitors as a power source rather than a cumbersome power line to a more stable remote power supply. Further, using such shutters in a welding helmet and in other environments where there is not a convenient access to a power supply connection directly to a utility company, battery power ordinarily must be used to drive the shutter. The power level, charge, energy, etc., of such batteries or rechargeable capacitors is depleted as the shutter is used or stored over time.

Prior shutter devices and circuits for use in automated welding lens systems have suffered from reduced switching performance or unstable transmission as the portable power supply's power level is depleted. Further, the power supply is depleted gradually causing the performance to deteriorate gradually allowing a safety hazard to gradually appear. The welder has to check the power level of the power supply to ensure that there will be no safety hazard from using the shutter after the power level is depleted to a point that performance can no longer be sustained at a safe level.

It is desirable to have a shutter device to protect the welder's eyes that has stable performance regardless of the power level input from a depletable power supply. Further it is desirable that when the power supply is depleted to a point where the device no longer performs to that intended or to a safe level, a highly visible signal will warn the welder.

BRIEF SUMMARY OF THE INVENTION

The present invention provides a driving circuit for a liquid crystal shutter or for other devices that provides a regulated voltage output from an unregulated or a depletable power source. This feature ensures that the performance of the shutter device will be consistent regardless of the charge level or the age of the power supply.

Another aspect of the invention is a low voltage indicator, such as a low battery voltage indicator, to indicate when battery (or other power source, hereinafter simply referred to as battery for convenience) voltage is low and the battery should be changed. This feature serves as a warning device to the welder or user that the device will soon not perform to the product specification or that the performance has degraded below an expected or acceptable level.

The features of the invention, as are described herein, may be employed in optical shutters and in connection with other devices, too.

The foregoing and other objects, features, aspects and advantages of the present invention will become more apparent as the following description proceeds. It will be appreciated that while a preferred embodiment of the invention is described herein, the scope of the invention is to be determined by the claims and equivalents thereof.

Also, the power supply circuits described in detail include a number of features, which preferably are useful together and also may be used independently in other circuits and devices. Further, features of one embodiment may be used in the other(s) embodiments disclosed herein, as will be evident.

To the accomplishment of the foregoing and related ends, the invention, then, comprises the features hereinafter fully described in the specification and particularly pointed out in the claims, the following description and the annexed drawings setting forth in detail certain illustrative embodiments of the invention, these being indicative, however, of but several of the various ways in which the principles of the invention may be suitably employed.

DETAILED DESCRIPTION

Figure 1:
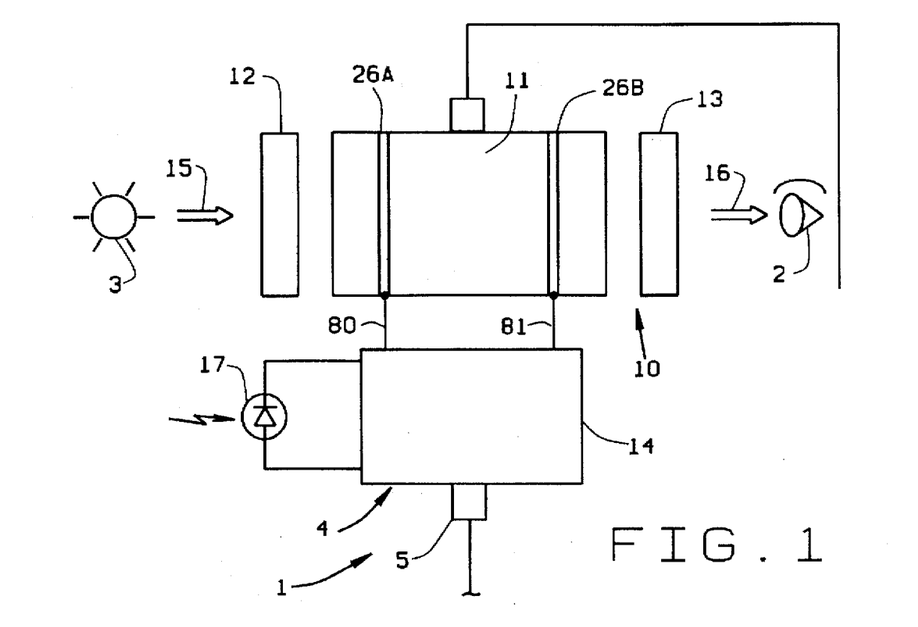
FIG. 1 is a schematic illustration of a liquid crystal optical shutter used in a welding helmet with a driving circuit therefor in accordance with the present invention.

Referring in detail to the drawings, wherein like reference numerals designate like parts in the several figures, and initially to FIG. 1, a welding helmet 1 (or equivalent protective eye gear) for wearing on the head of a person to protect the eyes 2 of a person from bright light emitted by a welding process represented as light source 3 is illustrated. Mounted in an opening 4 by a mounting mechanism 5 is an exemplary welding lens or liquid crystal shutter 10, which includes one or more variable optical retarders 11 (each preferably) sandwiched between a pair of linear polarizers 12, 13. The optical axes of the polarizers 12, 13 may be at right angles to each other and at 45 degrees to the optical axis of the retarder 11 as is described in the above-mentioned patents and patent application. The retarder 11 may be of the type disclosed in the above-mentioned patents and patent applications. Other types variable retarders also may be used. Other alignments of the components also may be employed, as may be desired to obtain the desirable operation of the shutter 10. If desired, more than one retarder may be used and more than one pair of polarizers may be used. Further, various other optical components, such as quarter wave plates, compensators, filters, devices to prevent scratching or to block dirt from the other components, etc., can be used in the shutter 10. Non-limiting examples of the above-mentioned parts are described in the above patents and patent applications. The shutter 10 may be used as a lens in a welding helmet, goggles or other eye protection device as well as in other devices intended to be protected from light or other electromagnetic energy which can be attenuated by the shutter. The shutter 10 may be a part of a welding lens system such as the ones disclosed in the above mentioned patent applications.

A power supply 14 according to the invention is operative to provide an electric field of prescribed voltage to the retarder 11 to determine how much of the input light 15 is transmitted as output light 16 by the shutter 10. A photosensitive detector 17, for example, in the form of a photosensor arrangement, such as one or more silicon photodetectors (although other photosensors may be used), detects the intensity of the incident light 15 and provides a control input to the power supply 14 which automatically operates the shutter 11. An exemplary detector 17 including redundant photosensors and associated circuitry is disclosed in the above patent application. Accordingly, when welding is not detected, input light 15 is at relatively low intensity, and substantially all of the light possible will be transmitted by the shutter 10 as output light 16. It will be appreciated that since polarizers and possibly other optical components are used in the shutter 10, it is likely that approximately 50% or more of the incident light 15 will be blocked by such polarizers in the clear state, as is described in the above referenced patent application. On the other hand, when welding is detected, the driving circuit 14 operates the shutter 10 to reduce, preferably, substantially below 50%, the relative intensity of the output light 16, i.e., relative to the intensity of the incident light 15, e.g., to several percent, preferably less than 1%, and more preferably to even less. (Ordinarily, maximum transmission may be limited to about 50% due to the use of polarizers unless special designs are used in the shutter, e.g.; a variable polarizer, as is described in one or more of the above patent applications.)

It will be appreciated that various types of photosensitive detectors 17 and associated circuitry may be used in connection with the power supply 14 and liquid crystal shutter 10 in addition to that which is described in detail herein. It also will be appreciated that other types of detectors or sensors may be employed to provide an input or to provide information to the power supply circuit 14 to cause appropriate operation of the liquid crystal shutter 10. Examples are electrical sensors which sense the electrical energy used to undertake welding and temperature sensors that may be used to sense the change in temperature due to welding. Another sensor would be a flow sensor that detects the flow of a gas used during a welding process. Other types of sensors also may be used, as will be appreciated to those having ordinary skill in the art.

Figure 2A:
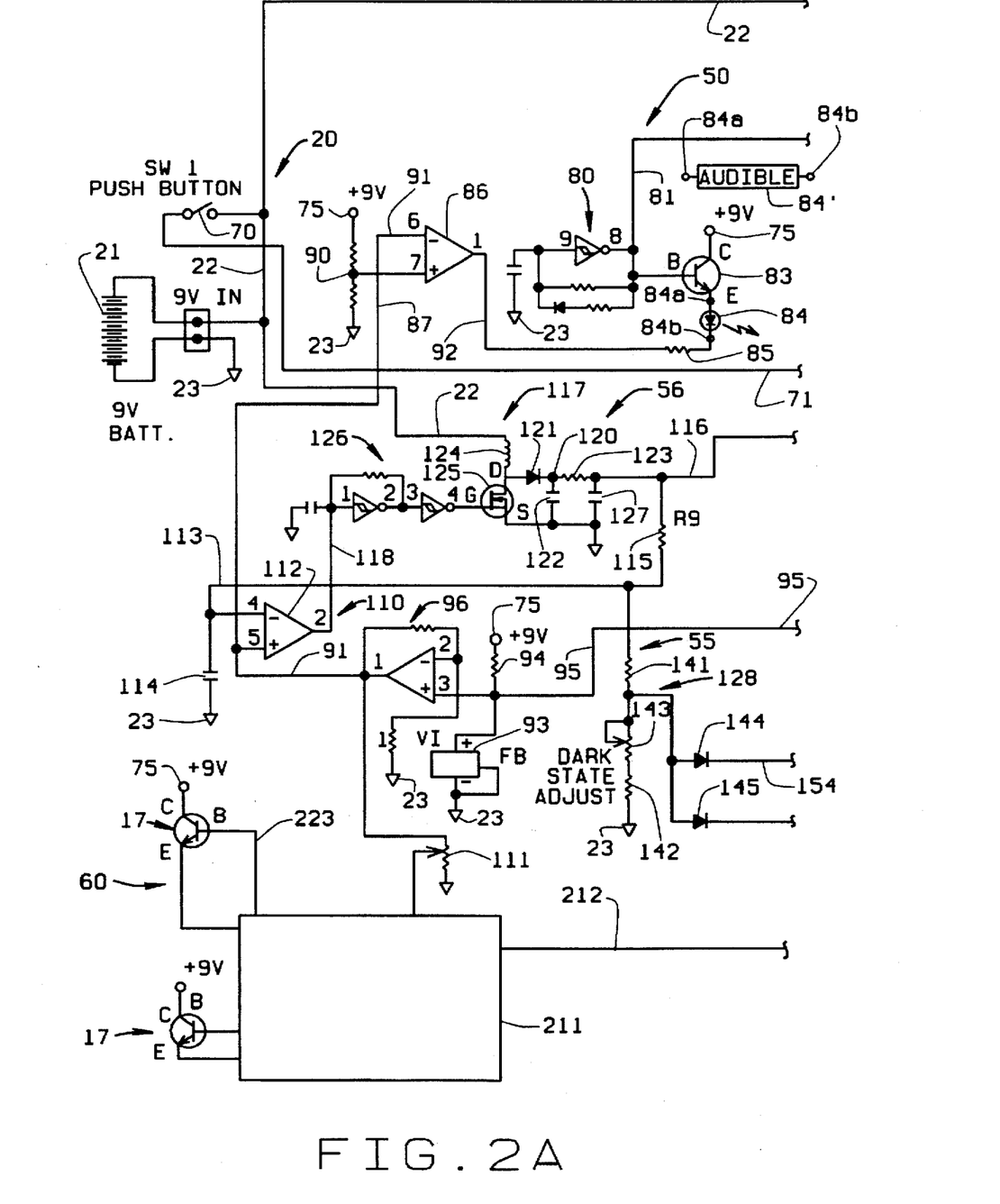
FIGS. 2A, 2B and 2C sometimes collectively referred to as FIG. 2 for convenience) is a schematic electric circuit diagram of a power supply and driving circuit employing the driver electronics according to the invention used with the liquid crystal shutter of FIG. 1.
Figure 2B:
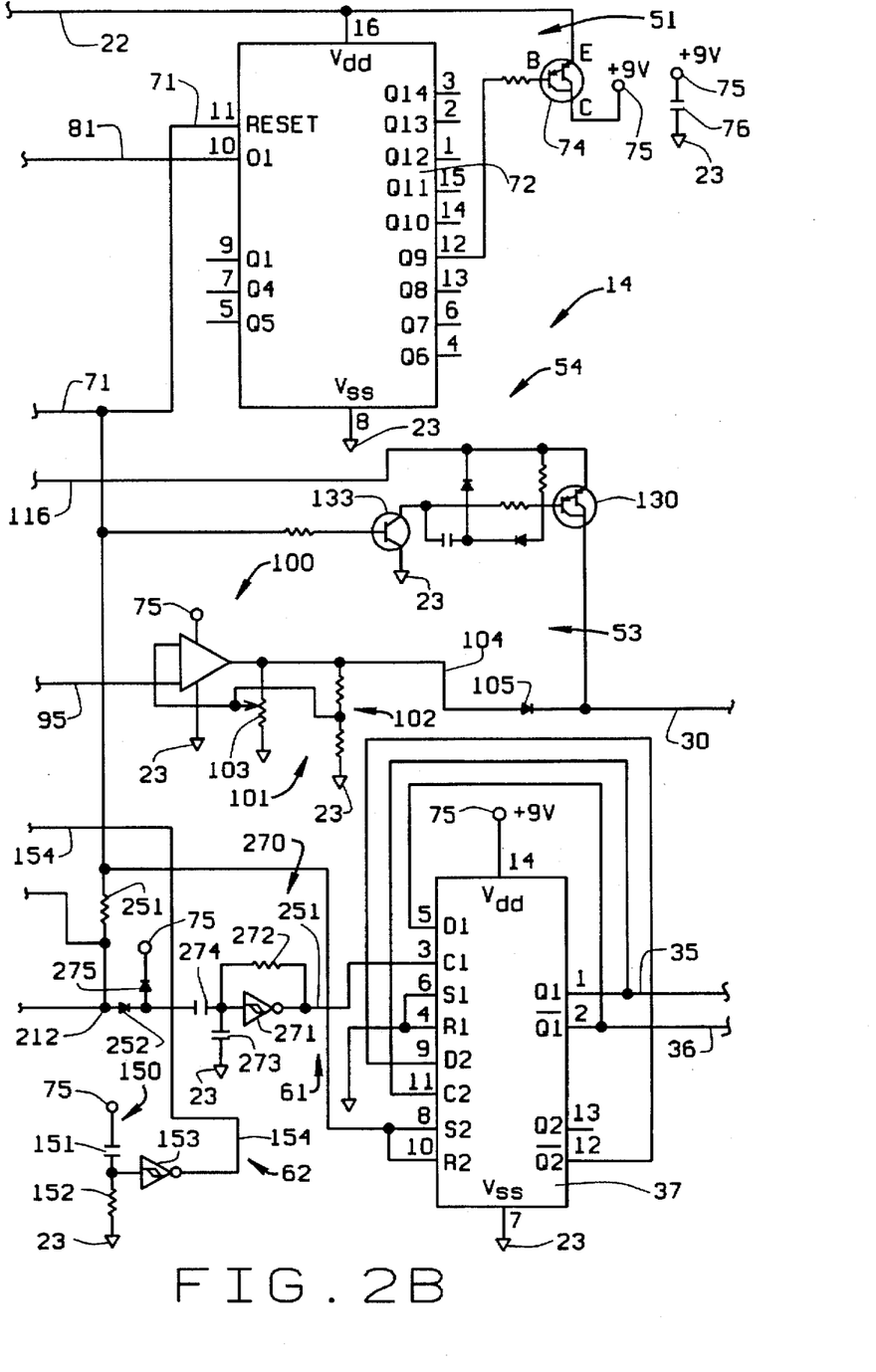
Figure 2C:
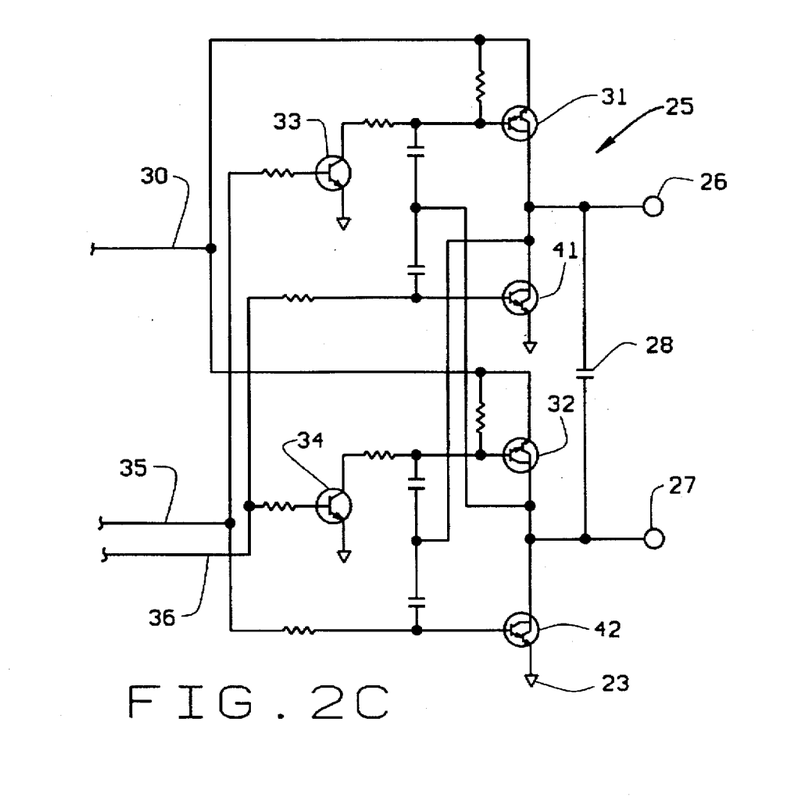

Turning to FIG. 2, a schematic electric circuit diagram of one embodiment of the power supply circuit 14 is illustrated. A number of details of the power supply 14 are described more fully in the parent application; and several of these are presented here in block diagram form and are summarized herein. A number of parts illustrated here are only briefly mentioned, and a more comprehensive description is presented in the parent application, which is incorporated by reference.

The power supply 14 includes an input circuit 20 where input electrical power is provided the power supply 14, for example, from a 9 volt electrical storage battery 21, which is connected between a positive electrical line or connection 22 and a negative or relative ground potential line or connection designated 23 at the left hand side of FIG. 2 and elsewhere in the drawing. Other types of power supplies also may be used; a non-limiting example is a solar cell or a light sensitive device that produces electrical energy; a capacitor or other storage system, etc. Larger or smaller magnitudes of voltage than the 9 volt battery 21 illustrated can be used. Also, if desired, the power supply may be provided via a transformer connection and/or via a direct connection to a source of electrical power, such as a battery, capacitor, alternator, generator, the electrical lines from the utility company, etc. The detector 17 indicates to the power supply 14 whether welding has been detected.

In the description hereof, reference to lines, leads, conductors, etc., essentially means an electrically conductive path from one place or device to another regardless of whether a discrete electrical wire is used for effecting the electrical connection; a printed circuit electrically conductive trace on a printed circuit board is employed to make that connection; implementation is within an integrated circuit where the connection is made; etc., without limitation. Furthermore, reference to logic 0 signal, ground reference potential, negative signal, etc., typically means the same, for example, a connection to the ground terminal 23 associated with the battery 21, or a typical logic 0 signal, as is well known in the electronics and digital circuitry field. Reference to a logic 1 signal typically means a positive (or negative, as the case may be) signal, such as that at the positive side of the battery 21, such as 9 volts, or some other value, even a relatively reduced value, but in any event a value that is distinguishable from the logic 0 signal level. These conventions are, of course, well known in the electronics art. Other conventions also may be employed consistent with the spirit and scope of the present invention.

Power Output Circuit 25

The power supply circuit 14 includes a number of portions which are operational in response to receiving power from the input circuit 20 to derive a voltage that the power supply circuit provides on the input power line 30 and complementary alternating signals that are provided on lines 35, 36, e.g., from a flip-flop 37 or other device, to operate the power output circuit 25. The power output circuit 25 in turn drives the liquid crystal shutter 10, which is connected to output terminals 26, 27.

During operation of the power output circuit 25, the power supply circuit 14 provides a voltage on line 30, which may be considered the power voltage for driving the variable retarder 11. The magnitude of that power voltage is controlled by the power supply circuit 14 to be relatively low during the clear state of the shutter 10; relatively higher during the dark state of the shutter 10; and temporarily to be even higher than the latter case when the shutter initially is driven from the clear state to the dark state. When the power supply circuit 14 is deenergized, or in some similar quiescent state, the power voltage on line 30 may be zero. The power voltage is supplied to the power terminals of output transistors, such as Darlington pair transistors 31, 32, 41, and 42 or other devices which couple such power to the retarder 11 to effect the desired operation thereof, e.g., in the manner illustrated in FIG. 2C. Under control of the transistors 33, 34, the respective Darlington power transistors supply effective AC voltage to the retarder 11.

Further, during operation of the power output circuit 25, complementary alternating signals, e.g., control signals, are provided by the power supply circuit 14 on lines 35 and 36, respectively. Such control signals also are supplied to the control or drive terminals of the output transistors or other devices in the power output circuit 25 selectively to control delivery of the power voltage to the retarder 11. As is described in greater detail in the parent application, when the shutter 10 is operated in the clear state, e.g., at relatively low power voltage, the control signals are provided on lines 35 and 36 at a relatively high frequency to avoid the appearance of flicker in the shutter. However, when the shutter 10 is driven to and operated in the relatively dark state, the frequency of the control signals is lower, which saves power and does not cause noticeable flickering because of the low transmission of light during the dark state of the lens.

A number of the above-mentioned portions of the power supply circuit 14 include a low supply voltage indicator circuit 50; time out circuit 51; power developing circuit 52, which includes a low voltage drive circuit 53 and a high voltage drive circuit 54, that provides the voltage on input power line 30; a regulated low voltage power supply and voltage reference circuit 55; a high voltage power supply 56; a sensor circuit 60 included as part of the detector 17; a frequency varying circuit 61 for determining the frequency of the flip-flop 37 and the alternating complementary signals on lines 35, 36 coupled to the output thereof; and a start/initialization circuit 62. These various circuits and circuit portions will be described in greater detail below and portions also are described in the parent application.

The description herein is directed to use of the power supply circuit 14 for developing a relatively low voltage AC signal for driving or powering the liquid crystal shutter 10 to the clear state and two relatively higher or larger magnitude AC electrical signals respectively for initially driving the shutter to the dark state and then for maintaining the shutter in the dark state. The circuit 14 also provides for varying the frequency of the driving signal to the shutter to minimize power usage in the dark state and to avoid flicker in the clear state. However, various features of the power supply circuit 14 may be used for providing power to operate other types of liquid crystal devices, such as shutters, displays or other devices; devices other than liquid crystal ones, and so forth.

Input Circuit 20, Low Supply Voltage Indicator Circuit 50, and Time Out Circuit 51

Power terminals 75 are shown throughout FIG. 2; these power terminals receive voltage from the battery 21 (or from some other power source) via connections (not shown) to line 22 or by other connection to the power source. The input circuit 20 includes a momentary contact start or on switch 70 or equivalent. Closure of the switch 70 provides a signal on line 71 to reset a counter 72 to start a counting sequence to maintain the circuit 14 operating until welding has not been detected for a prescribed time. (If welding has not been so detected, then the power supply circuit 14 preferably automatically shuts down to a quiescent or off state.) While the counter 72 is counting, i.e., before it times out, it provides an input to Darlington pair transistors 74 to couple power on line 22 to the various power terminals 75 for operation. When the counter 72 times out, the transistors 74 are turned off as is the rest of the circuit 14. The low supply voltage indicator circuit 50 and time out circuit 51 include an oscillator 80 coupled by line 81 to provide a counting or frequency signal to the counter 72 and to the base of a transistor 83. The collector and emitter junction of the transistor 83 is connected between the circuit power terminal 75 and a light emitting diode 84. The diode 84 is connected at terminals 84a, 84b, as is illustrated.

The diode 84 is intended to flash when the battery 21 or other power source voltage drops below a predetermined suitable value for desired operation in the power supply circuit 14. The diode 84 is connected via a resistor 85 to the output of a comparator amplifier 86, which detects whether the battery voltage is so low as to cause the diode to emit flashes of light. As alternatives or additions to the light emitting diode 84, an audible signal indicator 84' and/or a light source may be used.

The comparator 86 receives the battery voltage from terminal 75 via a resistor divider circuit 90 that is coupled to the non-inverting input and a regulated voltage on line 91, which is supplied from the regulated low voltage power supply and voltage reference 55 to the inverting input. The regulated voltage on line 91 is accurately maintained by the circuit 55 to a prescribed level. As long as the battery voltage at terminal 75 is of adequate magnitude, the comparator 86 will produce a logic 1 signal at its output 92 to block conduction through the diode 84. However, if the battery voltage at terminal 75 drops below a minimum magnitude, which is determined by the resistor divider 90 and the magnitude of the signal on line 91, the output from the comparator 86 switches to a logic 0 level (or effectively to ground reference potential), whereupon conduction through the diode 84 is unblocked. In the latter circumstance the oscillating signal on line 81 from the oscillator 80 will cause the transistor 83 in the low supply voltage indicator circuit 50 to oscillate between conduction and non-conduction, whereupon an oscillating current will flow through the diode 84 causing the diode 84 to emit a blinking light output. Such blinking light output indicates that the voltage magnitude provided by the battery 21 is below minimum magnitude for proper operation of the power supply circuit 14.

In the regulated low voltage power supply and voltage reference circuit 55 a voltage reference device 93 is connected in circuit with the battery terminal 75, resistor 94, and ground 23. The voltage reference device may be an LM385 which produces a 1.23 volts output; or it may be another device which provides the same or a different regulated voltage output. An alternate device may be a zener diode. The voltage on line 95 is relatively accurately regulated by the reference 93, and such regulated reference voltage is supplied both via an amplifier 96 to line 91 and directly via line 95 to an input of the low voltage drive circuit 53.

Thus, it will be appreciated that low supply voltage circuit 50 compares the supply voltage or a signal or information representing it with another voltage, such as a fixed reference voltage, some other voltage, or a signal or information representing it. When the comparison, whether by a comparator amplifier, divider circuit, bridge circuit, or some other means, indicates the former signal (e.g., supply voltage) is too low, then an indicator thereof is initiated. Such indication may be by emitting of a constant light output, e.g., from the light emitting diode 84, flashing of that diode, which is more attention gaining, or by some other indicator, as may be desired.

Low Voltage Drive Circuit 53

In the low voltage drive circuit 53, mostly shown in FIG. 2B and also partly shown in FIG. 2A, an amplifier 100 receives the regulated reference voltage on line 95. The amplifier 100 has a feedback circuit 101, which includes a resistor divider 102 and an adjustable potentiometer (variable resistor) 103. In response to the regulated reference voltage input on line 95 and adjustment of potentiometer 103, the amplifier 100 produces on its output line 104 a voltage (e.g., from about two volts to about four volts) that is of a magnitude intended to maintain the shutter 10 in the clear state. The potentiometer 103 may be adjusted manually (or otherwise) to adjust the actual voltage on line 104 so that such voltage is the desired voltage for maintaining the clear state of the shutter 10. The voltage on line 104 is supplied via blocking diode 105 to the input power line 30. The blocking diode 105 prevents voltage from the high voltage drive circuit 54 from feeding to the low voltage drive circuit 53. Ordinarily it is expected that the voltage on line 95 will be maintained relatively accurately as a function of the voltage reference 93 as long as the voltage at battery terminal 75 exceeds a minimum voltage value. If the battery 21 does not supply the minimum voltage value, then the low supply voltage indicator circuit 50 will cause the diode 84 to flash.

The amplifier 96 boosts the reference voltage signal from the regulated voltage source 93 received on line 95. The amplifier 96 also provides adequate sourcing capability to provide the necessary input to three circuits in the power supply 14, as follows. The regulated voltage on line 91 at the output from the amplifier 96 is supplied to the comparator 86 in the low supply voltage indicator circuit 50, which can indicate that the supply voltage is too low by flashing the diode 84. The regulated voltage on line 91 also is supplied to a comparator input circuit 110, which is associated with the high voltage power supply 56. The regulated voltage on line 91 further is coupled via an adjustable potentiometer 111 to the sensor circuit 60.

High Voltage Power Supply 56 and High Voltage Drive Circuit 54

The comparator input circuit 110 provides an electrical input to the high voltage power supply 56 and includes a comparator amplifier 112, which has its non-inverting input coupled to line 91 to receive the amplified regulated voltage, and which has its inverting input coupled to line 113. Line 113 is coupled via a capacitor 114 to ground 23 and via a resistor 115 to the power output line 116 of a high voltage switching DC to DC power supply circuit 117. When the voltage on line 113 is less than the voltage on line 91, the comparator amplifier 112 produces a signal on line 118 to energize the switching power supply 117 to develop a relatively high voltage level at the junction 120 of a diode 121, capacitor 122 and resistor 123, as is seen in FIG. 2. Preferably the high voltage power supply 56 receives the 9-volt battery voltage on line 22 and it is operative using the inductor 124, field effect transistor (MOSFET) 125, diode 121, capacitor 122, and input amplifier circuit 126 to develop at the junction 120 a relatively high voltage signal suitable to drive the shutter 10 in the dark state. Capacitor 114 adds stability to the circuit by decoupling noise on line 113 from reaching the comparator 112.

More particularly, the high voltage power supply circuit 56 uses the input amplifier circuit 126 to develop a square wave signal, for example at 100 KHz or some other suitable frequency, to drive the MOSFET 125 to provide rapid switching for the inductor 124. A voltage developed by the inductor 124 and transistor 125 is delivered via the diode 121 for storage in the capacitor 122. Resistor 123 and capacitor 127 provide an RC filter and storage function. The inductor 124 charges the capacitor 122 through the diode 121 as a conventional LC circuit; and the capacitor 122 tends to maintain a voltage level thereon at about 40 volts or some other maximum to drive the shutter 10 from clear to dark state or at some other voltage, e.g., on the order of from about 10 to about 20 volts (or some other voltage), determined by a dark state adjustment resistance divider circuit 128 to maintain the shutter 10 in the dark state, as is described below. The dark state adjustment circuit provides for adjustment of the dark state or lesser light transmission characteristic of the shutter 10 over a range determined at least in part by the magnitudes of the resistances therein. The actual magnitude of the signal on line 116 at the output of the high voltage power supply circuit 56 can be adjusted as a function of the magnitudes of the various components in the circuit, as will be appreciated by those having ordinary skill in the art and as is described further below. Delivery of the voltage on the power output line 116 from the high voltage drive circuit 54 to the input power line 30 of the power output circuit 25 is controlled by Darlington pair power transistors 130 (or equivalent), control transistor 133, and associated circuitry illustrated.

To determine the magnitude of the voltage at line 116 from the high voltage power supply 56, the voltage divider circuit 128 can be selectively switched by selective blocking or unblocking of diodes 144, 145. When the cathode of either diode 144, 145 is coupled to a source of ground reference potential, such diode is unblocked. Such unblocking may be provided by the start/initialization circuit 62 or by the sensor circuit 60. If either diode 144, 145 is unblocked, then it effectively short circuits or bypasses the potentiometer 143 and resistor 142. Therefore, for a given voltage on line 116, the voltage on line 113 will be less than it would be if such potentiometer 143 and resistor 142 were not bypassed. Accordingly, the comparator 112 will operate the high voltage power supply circuit 56 to strive to produce a maximum voltage at output junction 120, at, for example, from about 30 volts to about 50 volts, preferably about 40 volts.

However, when both diodes 144, 145 are blocked by logic 1 signals at their cathodes, the potentiometer 143 and resistor 142 are operatively in circuit with the resistors 115, 141; and the proportion of the voltage on line 116 which appears on line 113 increases. Therefore, the voltage produced at the output junction 120 and on line 116 is reduced, for example, to about 10–20 volts. The storage capacity of the capacitor 127 prevents immediate change between the very high, say 40 volts, and lower, say 19 volts, output from the high voltage power supply circuit 56.

The high voltage 40 volt signal expedites switching of the shutter 10 to the dark state. The lower 10–20 volt signal is adequate to maintain the dark state thereafter. The voltage reduction reduces power draw on the battery 21. It will be appreciated that the high voltage and maintenance voltage may be other than those described herein, e.g., depending on circuit component values, shutter requirements, etc.

The start/initializtion circuit 62 includes an RC charging circuit 150, having a capacitor 151 and a resistor 152, and a Schmitt trigger circuit 153. The output line 154 from the Schmitt trigger circuit 153 is coupled selectively to unblock the diode 144 when the power supply circuit 14 is turned on upon closure of the switch 70; unblocking of the diode 144 assures that the high voltage power supply 56 will provide maximum voltage to the line 116. After the start/initialization circuit 62 has charged suitably, it will block the diode 144.

Sensor Circuit 60

The sensor circuit 60 includes one or more, e.g., for redundancy, photosensitive or photodetector circuits 200, which produce on line 212 a logic 0 signal when welding has not been detected and a logic 1 signal when welding has been detected. A time delay for transitioning from switching from the condition of detecting welding to not detecting welding may be included in the sensor circuit 60 to prevent such switching when detection of welding is lost only for a relatively brief time. Details of the sensor circuit 60 are described in the parent application which are incorporated herein by reference. Also, variable feedback control of the sensor circuit 60, which is described in detail in the parent application, may be used to sensitize the sensor circuit 60 for the particular ambient light conditions so that welding can be properly promptly detected when it occurs.

Frequency Varying Circuit 61

The frequency varying circuit 61 includes an oscillator 270 formed by a Schmitt trigger circuit 271, feedback resistor 272, and one or both capacitors 273, 274. The capacitor 273 is connected to ground 23. When welding is not detected, the resistor 272 and capacitor 273 determine the time constant for the oscillator 270. Such time constant is relatively fast, for example, causing the oscillator 270 to produce an output signal having a frequency on the order of 40 Hz, although the actual frequency may be larger or smaller. Preferably the frequency is adequate to minimize power required for driving the shutter 10 while avoiding flicker. The output from the oscillator 270 is provided via line 252 as an input to drive the flip-flop 37.

When the sensor circuit 60 detects welding and provides a logic 1 signal on line 212, the diode 252 becomes conductive and effectively adds the capacitor 274 operatively in circuit connection with the capacitor 273 and resistor 272 for the oscillator 270. Adding such capacitor 274 in such circuit causes the oscillator 270 to reduce the frequency in the output signal produced thereby on line 252, e.g., to several Hz. The reduced frequency signal drives the flip-flop 37 at a reduced frequency so that the shutter is driven at a reduced frequency. As a result, the power required to drive the shutter is reduced. Also, since the shutter then is operating in the dark state, any problem due to flicker is avoided. Diode 275 connected to the battery positive terminal 75 provides for discharging of the capacitor 274 after welding no longer is detected by the sensor circuit.

SUMMARY OF OPERATION OF POWER SUPPLY 14 WITH SHUTTER 10

When the momentary contact power switch 70 is closed, the time out circuit 51 is reset to count for 15–16 minutes, and battery voltage is provided terminal 75 until the time out circuit shuts down the power supply circuit 14. If the voltage of battery 21 is below a prescribed minimum, the light emitting diode 84 will flash. Upon closing the switch 70, the start/initialization circuit 62 will unblock diode 144 so that the high voltage power supply circuit rapidly will charge to its maximum high voltage level of, say, 40 volts ready to drive the shutter 10 to the dark state. The closed switch 70 will turn on transistor 133 to conduction, which, in turn, turns on the Darlington Pair transistor 130; and the latter then supplies the high voltage from line 116 of the output of the high voltage power supply circuit 56 to the shutter 10 to set up the directors, e.g., alignment of liquid crystal structure, in the variable retarder 11. After the capacitor 151 in the start/initialization circuit 62 charges adequately so that the diode 144 becomes unblocked, if welding has not yet occurred, there will be a logic 0 signal at line 212 from the output of the sensor circuit 60. Such logic 0 signal maintains diode 145 unblocked so that the voltage at line 116 will remain at maximum; and such logic 0 acting through transistor 133 also maintains the high voltage drive circuit 54 cut off by preventing conduction in Darlington pair transistors 130. If welding has not yet been detected after the capacitor 151 charges adequately to disable the start/initialization circuit 62, then the low voltage drive circuit 53 provides a voltage through the diode 105 to maintain the shutter in the clear state. However, when welding subsequently is detected (or if welding were detected while the start/initialization circuit still were in its initialization mode unblocking diode 144), a logic 1 signal is produced on line 212 to turn on the high voltage drive circuit 54, which then delivers the initial high voltage from line 116 to the power output circuit 25 to expedite turn on of the shutter to the dark condition. The logic 1 signal on line 212 also blocks diode 145 so that after the high voltage at line 116 drives the shutter 10 to the dark state, such voltage will drop to the reduced dark state maintenance voltage level to maintain the shutter in the dark state. The frequency of the shutter drive signal at terminals 26, 27 will be a function of the frequency varying circuit 61, which produces a high frequency signal when clear state is required and a lower (but non-zero to avoid polarizing the liquid crystal and/or other detrimental affects) frequency signal when dark state is required.

ALTERNATE EMBODIMENT

Figure 3:
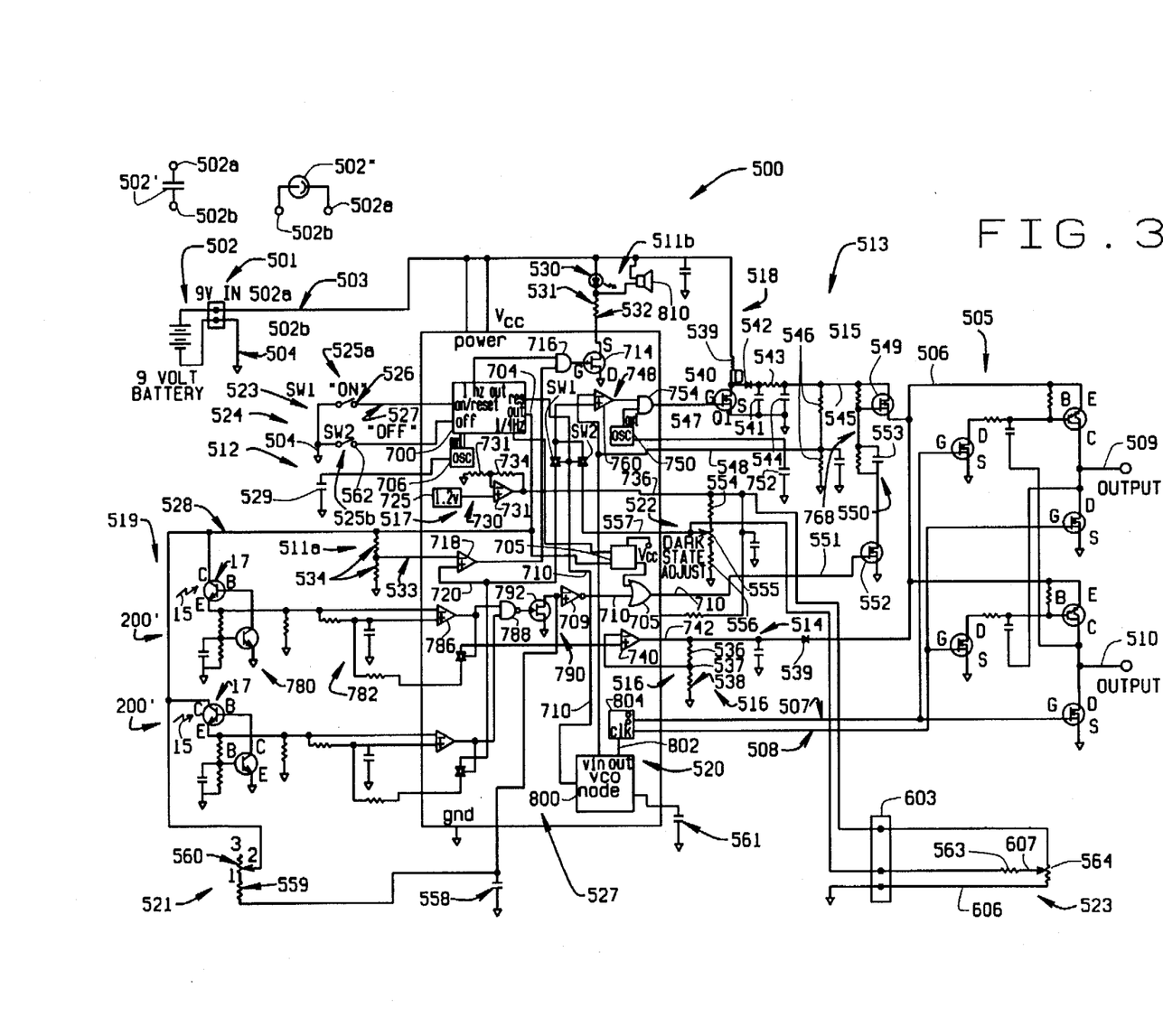
FIG. 3 is a schematic illustration of an alternate embodiment of the power supply and driver circuit with numerous functions substantially integrated into a single integrated circuit or other silicon electronic device.

Referring to FIG. 3, an alternate power supply 500 according to the invention is illustrated. The power supply 500 may be substituted for the power supply circuit 14 of FIG. 2, and it is operative to provide an electric field of prescribed voltage to the retarder 11 to determine how much of the input light 15 is transmitted as output light 16 by the shutter 10. A photosensitive detector 17, for example, in the form of a photosensor arrangement, such as one or more silicon photodetectors (although other photosensors may be used), detects the intensity of the incident light 15 and provides a control input to the power supply 500 which automatically operates the shutter 11. Accordingly, when welding is not detected, input light 15 is at relatively low intensity, and substantially all of the light possible will be transmitted by the shutter 10 as output light 16. It will be appreciated that since polarizers and possibly other optical components are used in the shutter 10, it is likely that approximately 50% or more of the incident light 15 will be blocked by such polarizers in the clear state, as is described in the above referenced patent applications. On the other hand, when welding is detected, the power supply circuit 500 operates the shutter 10 to reduce substantially below 50% the relative intensity of the output light 16, i.e., relative to the intensity of the incident light 15, e.g., to several percent, preferably less than 1%, and more preferably to even less.

It will be appreciated that various types of photosensitive detectors and associated circuitry may be used in connection with the power supply 500 and liquid crystal shutter 10 in addition to that which is described in detail herein. It also will be appreciated that other types of detectors or sensors may be employed to provide an input or to provide information to the power supply circuit 500 to cause appropriate operation of the liquid crystal shutter 10. Examples are electrical sensors which sense the electrical energy used to undertake welding and temperature sensors that may be used to sense the change in temperature due to welding. Another sensor would be a flow sensor that detects the flow of a gas used during a welding process. Other types of sensors also may be used, as will be appreciated to those having ordinary skill in the art.

In FIG. 3 a schematic electric circuit diagram of the integrated power supply circuit 500 is illustrated. The power supply circuit 500 is operative to supply functions substantially similar to those provided by the power supply 14, as are described above; therefore, circuit portions that are substantially similar are understood to be as above described unless specifically mentioned hereinbelow. The power supply circuit 500 sometimes is referred to herein as an integrated power supply because much of the circuitry thereof is combined using conventional integrated circuit fabrication techniques for inclusion in a single (or possibly in several) integrated circuit for operation in conjunction with the other circuit portions shown in FIG. 3. A person having ordinary skill in the art of integrated circuit design would be able to build such an integrated circuit using the teachings described herein.

The power supply circuit 500 includes an input circuit 501 where input unregulated electrical power is provided the power supply, for example, from a 9 volt electrical storage battery 502, which is connected by terminals 502a, 502b between a positive electrical line or connection 503 and a negative or relative ground potential line or connection designated 504 at the left hand side of FIG. 3 and elsewhere in the drawing. Other types of power supplies also may be used having larger or smaller magnitudes than the 9 volt battery indicated. Also, if desired, the power supply may be provided via a transformer connection and/or via a direct connection to a source of electrical power, such as a battery, capacitor, alternator, generator, the electrical lines from the utility company, etc. Exemplary unregulated power sources that may be substituted for the battery 502 or used simultaneously in connection therewith, include the illustrated capacitor 502' and/or the solar (or other photosensitive or equivalent) cell 502".

The power supply circuit 500 provides power and control signals to operate the power output circuit 505, which in turn drives the liquid crystal shutter 10. More specifically, the circuit 500 includes a number of portions which are operational in response to receiving power from the input circuit 501 to derive the voltage on the input power line 506 and the complementary alternating signals on lines 507, 508 to control power application to terminals 509, 510 to drive the shutter 10. A number of those portions are a low supply voltage indicator circuit 511; a time out circuit with manual bypass 512; power developing circuit 513, which includes a low voltage drive circuit 514 and a high voltage drive circuit 515, that provides the voltage on input power line 506; a regulated low voltage power supply 516 and voltage reference circuit 517; a high voltage power supply 518; a sensor circuit 519 having redundant photodetector circuits 200'; a frequency varying circuit 520 for determining the frequency of the alternating complementary signals on lines 507, 508 coupled to the output thereof; a variable delay circuit 521; a dark state voltage adjustment circuit 522 with detachable fine tuning circuit 523; and a start/initialization circuit 524. These various circuits and circuit portions will be described in greater detail below.

The description herein is directed to use of the power supply circuit 500 for developing a relatively low voltage AC signal for driving or powering the liquid crystal shutter 10 to the clear state and two relatively higher or larger magnitude AC electrical signals respectively for initially driving the shutter to the dark state and then for maintaining the shutter in the dark state. The circuit 500 also provides for varying the frequency of the driving signal to the shutter to minimize power usage in the dark state and to avoid flicker in the clear state. However, various features of the power supply circuit may be used for providing power to operate other types of liquid crystal devices, such as shutters, displays or other devices; devices other than liquid crystal ones, and so forth.

Power Output Circuit 505

The power output circuit 505 has a pair of terminals 509, 510, which are connected to electrodes or the like which provide operating energy or power to the variable optical retarder 11 (or other liquid crystal device, or still other device, in general) of the liquid crystal shutter 10. Typically an AC electrical voltage is supplied across the terminals 509, 510, and those terminals are connected to electrodes that are at opposite sides of the variable optical retarder 11, for example, to provide an electric field across the liquid crystal material in the retarder. The power output circuit 505, provides an AC voltage signal to the variable optical retarder 11. The magnitude or amplitude of the AC voltage signal is determined by the voltage on input power line 506, and the frequency and phase of the AC voltage signal is determined by the alternating control signals on output control lines 507, 508.

Start/Initialization Circuit 524, and Time Out Circuit 512

The start/initialization circuit 524 includes a momentary contact (start) switch 525a, which is coupled between negative line 504 (negative because it is coupled to the negative terminal of the battery 502) and to a on/reset input line 526 of the integrated circuit 527 (which contains a portion of the time out circuit 512). A brief closure of the switch 525 resets a counter 700 in the integrated circuit 527 whereby the output of the counter (designated 704) provides power to all internal portions of integrated circuit 527 and provides a high output on line 528 to power all external components placing the power supply circuit in the on state. When the counter 700 is reset, the counter output 704 is a digital "1" or "high" signal and the voltage on line 528 is substantially equal to the $V_{cc}$ voltage of the counter 700, e.g., the battery 502 voltage. When the counter 700 reaches a prescribed count, the counter output 704 transitions to a digital "0", e.g., zero volts.

When the start/initialization circuit 524 is activated from a deenergized state by depression of the switch 525a, the counter 700 will begin to count a specified period of time (i.e., a prescribed number of pulses from an oscillator 706) as determined by the value of a timing capacitor 529, in this case approximately 30 minutes, or some other desired time. The counter output 704 transitions from low to high when the switch 525a is pressed and provides a logic "1" clock input to a D-type flip flop 705. The flip flop 705 has coupled to its D input the $V_{cc}$ supply. This results in a logic "1" being loaded into the flip flop 705 initially, indicating the beginning of an initialization period. The reset input of the flip flop 705 is coupled to a ¼ hertz output of the counter 700. The ¼ hertz output goes high 2 seconds after the counter 700 is initially reset via the switch 525a, signalling the end of the initialization period whereby the flip flop output is reset to a logic "0". The output of the flip flop is connected to an OR gate 705'. Since the logic level on the counter output 704 changes state only at power up and not during subsequent resets of the counter 700 via line 710 as discussed below, the Q output of the flip flop 705 will remain low following the initialization period. Thus, following the initialization period of 2 seconds, the OR gate 705' produces an output onto line 710 identical to the signal on line 710', both of which are referred to herein as line 710 for convenience.

During the initialization period, the logic "1" output of the flip flop 705 is ORed onto line 710 whereby the logic "1" output of the OR gate 705 causes the high voltage power supply 518 to provide via the power output circuit 505 a maximum voltage for the reasons described below, in this case about 40 volts or other desired voltage, suitable for driving the shutter 10 to the dark state ready for virtually immediate use, and also to expedite setting up the directors of the liquid crystal material in the variable retarder 11 for operation of the shutter. After this initial period is over, the output of the flip flop 705 goes low and the power supply circuit 500 will continue with normal operation as described below.

For the time out circuit 512, a free running oscillator circuit 706 contained within the integrated circuit 527 provides an AC signal whose frequency is determined by capacitor 529 to clock input of the counter 700 contained in the integrated circuit 527. In one embodiment, the frequency of the signal produced by the oscillator 706 and the number of pulses (counts) having to have been received by the counter 706 in order to produce the change in state of the power supply circuit 500 to the off state are selected to take a prescribed period of time, for example, about 30 minutes or other selected time. If the counter 700 reaches the prescribed number of counts before being reset by a signal on line 526, or by a change in state of the photodetector circuits 200', then the counter 700 will cause the internal portions of the integrated circuit 527 to be shut off and the output signal 528 to go to the logic 0 state as a result of the counter output 704 going low. This will cause the power supply circuit 500 to be deenergized.

The time out circuit 512 can be bypassed by a closure of the momentary switch 525b (i.e., a power off or stop switch). Closure of the switch 525b activates the off input of the counter 700, which disables the counter and sets the counter output 704 to a logic "0" state. If a switch closure is detected by the time-out circuit 512, then the power supply circuit 500 will be immediately deenergized. Therefore, it will be appreciated that if the power supply circuit 500 initially is energized by closing the switch 525a, but welding is not occurring, the time out circuit 512 automatically will turn off the power supply circuit 500 after the prescribed time that is determined as a function of the frequency of the signal produced by the oscillator 706 and the number of counts required by the counter 700 to provide a change in state thereof. If the stop switch 525b is closed, the circuit 500 will be immediately shut off, not requiring the usual 30 minute time out period, for example. If welding is being detected by the sensor circuit 519, a reset signal will be delivered to the time-out circuit 512 by the sensor circuit each time the state of the detector circuit changes. More specifically, a Schmitt invertor 709 in the sensor circuit 519 will deliver a reset signal on line 710 to a reset input of the counter 700.

Low Supply Voltage Indicator Circuit 511

The low supply voltage indicator circuit 511 comprises two portions 511a and 511b, referred to collectively as 511 for convenience. The low supply voltage indicator circuit 511 includes a light emitting diode 530 which is connected from line 503 through resistor 531 to the source of transistor 714. The drain of the transistor 714 is connected to ground, and a gate signal is provided by the output of AND gate 715.

One input of the AND gate 716 is connected to a one hertz output of the counter 700 which is provided, for example, from the output of an intermediate stage (not shown) in the counter 700, as can be the ¼ hertz output. The one hertz output alternates between a digital "1" and "0" level as is conventional. The other input of the AND gate 716 is connected to the output of a comparator 718. The comparator 718 compares a scaled value of the battery 502 voltage received on line 533 at the inverting input of the comparator 718 to a reference voltage provided received on line 520 at the non-inverting input. The scaled value of the battery voltage is provided by a resistor divider network 534 coupled between the counter output 704 on line 528 and ground. The reference voltage is a fixed regulated voltage provided by the voltage reference circuit 517 as is described below.

As long as the battery voltage at line 528 is of adequate magnitude, the scaled input on line 533 will be greater than the reference voltage output of the voltage reference circuit 517, and consequently the output of the comparator 718 will be a logic "0". As a result, the output of the AND gate 716 will remain low and the transistor 714 remains in an off, i.e., non-conductive state. The light emitting diode 530 therefore will not have any current passing therethrough and the light emitting diode 530 will not be activated. However, if the scaled battery voltage at line 533 drops below a minimum magnitude, as determined by the resistor divider 534 and the magnitude of the voltage reference circuit 517 on line 720, the output of the comparator 718 will go high to a logic level "1". The high output of the comparator 718 serves as a gating signal to gate the one hertz signal from the counter 700 through the AND gate 716. As a result, the output of the AND gate 716 will oscillate between a digital high and low value, thus causing the transistor 714 to oscillate between conduction and non-conduction. Accordingly, an oscillating current will flow through the light emitting diode 530 causing the light emitting diode 530 to emit a blinking light output at one hertz. Such a blinking light output indicates that the voltage magnitude provided by the battery 502 is below minimum magnitude for proper operation of the power supply circuit.

It will be appreciated that the frequency at which the light emitting diode 530 blinks can be any frequency as determined by the signal provided to the AND gate 716 from the counter 700. Moreover, any free-running oscillator can be used in place of the one hertz output provided by the counter 700 without departing from the scope of the invention. The voltage to which the battery 502 voltage can drop before the low voltage indicator circuit 511 causes the light emitting diode 530 to blink is a matter of choice and can be determined by way of the resistor divider 534 and reference voltage value as will be appreciated.

Voltage reference circuit 517

In the voltage reference circuit 517, a voltage reference device 725, such as a band gap reference circuit inside integrated circuit 527, produces a highly stable 1.20 volts regulated output. This regulated output does not change regardless of battery input voltage so long as the battery input voltage is of sufficient magnitude to support the voltage reference device 725. The output of the voltage reference device 725 is amplified by an amplifier 730 which includes an operational amplifier 731. The gain of the amplifier 730 is set by resistors 733, 734 as is conventional. In the embodiment of FIG. 3, the amplifier gain is three whereby the output of the operational amplifier on line 736 is 3.6 volts. The voltage on line 736 is relatively accurately regulated by the voltage reference circuit 517, and such regulated reference voltage is utilized inside the integrated circuit 527 by the low battery indicator circuit 511, the photodetector circuit 519, the high voltage power supply circuit 518, and the low voltage regulated power supply circuit 516 to provide consistent performance throughout the battery life.

Regulated low voltage power supply 516 and Low Voltage Drive Circuit 514

In the regulated low voltage power supply 516 and low voltage drive circuit 514, integrated circuit 527 contains an adjustable regulator circuit 516' which is based on the voltage reference circuit 517. The adjustable regulator circuit 516' has an amplifier and feedback circuit which includes operational amplifier 740 and resistors 536, 538. The reference voltage on line 736 is coupled to the non-inverting input of the amplifier 740, and feedback resistor 536 is coupled between the output of the amplifier 740 and its inverted input. The resistor 538 is coupled between the inverting input and ground, and the ratio of the resistors 536 and 538 determines the gain of the amplifier 740. Thus, based on the regulated reference voltage 517 and the values of resistors 536, 538, the regulator produces on its output on line 742 a voltage (e.g., about four volts or other desired voltage) that is of a magnitude intended to maintain the shutter 10 in the clear state. The voltage on line 742 is supplied via blocking diode 539 to the input power line 506. The blocking diode 539 prevents voltage from the high voltage drive circuit 515 from feeding to the low voltage drive circuit 514. Ordinarily it is expected that the voltage on line 742 will be maintained relatively accurately as a function of the reference voltage from the voltage reference circuit 517 as long as the voltage at battery terminal 503 exceeds a minimum voltage value.

It is noted that in the preferred embodiment the resistors 536 and 538 are external from the integrated circuit 527 and are connected thereto by corresponding integrated circuit pins or leads. Thus, the gain of the amplifier 740 can be adjusted easily if desired to provide the desired voltage on line 742.

High Voltage Power Supply 518 and High Voltage Drive Circuit 515

The high voltage power supply 518 receives the battery voltage on line 503 and it is operative using the inductor 539, field effect transistor (MOSFET) 540, diode 542, resistor 543, capacitors 541, 544 and control circuitry 748 contained within integrated circuit 527 to develop on line 545 a relatively high voltage signal suitable to drive the shutter 10 in the dark state. When the voltage on line 545 is less than the required voltage (as determined below), the control circuitry 748 produces a signal on line 547 to energize the switching power supply 518 to develop a relatively high voltage level line 545.

More particularly, the high voltage power supply control circuitry 748 includes a free running oscillator 750 which develops a square wave signal, for example at 100 KHz (or other suitable frequency as determined by external timing capacitor 752) and which is connected to an input of AND gate 754. The output of the AND gate 754 on line 547 drives the gate of MOSFET 540 to provide rapid switching for the inductor 539. A voltage developed by the inductor 539 and transistor 540 is delivered via the diode 542 for storage in the capacitor 541. Resistor 543 and capacitor 544 provide an RC filter and storage function. The inductor 539 charges the capacitor 541 through the diode 542 as a conventional LC circuit; and the capacitor 541 tends to maintain a voltage level thereon at about 40 volts or at some other voltage determined by a dark state adjustment resistance divider circuit 522, as is described below. The actual magnitude of the signal on line 545 at the output of the high voltage power supply circuit 518 can be adjusted as a function of the magnitudes of the various components in the circuit, as will be appreciated by those having ordinary skill in the art and as is described further below.

Moreover, a power saving feature of the high voltage power supply circuit 518 is that operation thereof to develop the relatively high voltage on line 545 only occurs in two cases. The first case is when the device 10 is in the clear state, and the control circuitry 748 detects that the voltage on feedback line 548 derived through the resistor divider circuit 546 is too low relative to the regulated low voltage on line 736. In particular, the control circuitry 748 includes a comparator 760 which compares the voltage on line 548 as provided to its inverting input to the reference voltage on line 736 coupled to its non-inverting input by an analog switch SW1. The switch SW1 is controlled via its inverted input by the detector circuit 519 output on line 710 which is low when the device 10 is in a clear state, causing the switch SW1 to be conductive. When the feedback voltage on line 548 drops below the reference voltage, the output of the comparator 760 goes high. As a result, the output of the oscillator 750 is gated through the AND gate 754 to drive the switching power supply 518 and charge the capacitor 541. As the feedback voltage on line 548 builds back up to a value equal to or greater than the reference voltage, the output of the comparator 760 goes low so as to mask the output of the oscillator 750 via the AND gate 754.

The second case occurs when the device 10 is in the dark state, and the control circuitry 748 detects that the voltage on line 548 is too low relative to the voltage derived from the dark state adjustment circuit 522 on line 557. More particularly, when the device 10 is in a dark state the logic level on line 710 is high. This causes switch SW1 to be in a non-conductive state and switch SW2 to be in a conductive state. Switch SW2 is operative to couple electrically the signal on line 557 to the non-inverting input of the comparator 760. The voltage level on line 557 is determined by the dark state voltage adjustment circuit 522 and the detachable/remote fine tuning adjustment 523 described below, and effectively determines the magnitude of the regulated high voltage on line 545 for maintaining the dark state of the shutter 10. When the scaled voltage on feedback line 548 drops below the voltage on line 557, the output of the oscillator circuit 750 is gated through to the switching power supply 518 to pump the inductor 539 and charge the capacitor 541. When the voltage on line 548 exceeds the voltage on line 557, again the output of the oscillator circuit 750 is blocked from the switching power supply 518.

Therefore, in both cases the high voltage switching power supply 518 is operated only when it is needed to provide and/or boost the voltage on line 545.

The high voltage on line 545 is selectively coupled to the input power line 506 via the high voltage drive circuit 515. The high voltage drive circuit 515 includes an output field effect transistor 549 and a control circuit 550 therefor. The control circuit 550 receives a signal on line 551 to the gate of a field effect transistor 552 when it is desired to provide the high voltage from line 545 to the input power line 506 in order to drive the shutter 10 to the dark state. The control circuit 550 is made up of a capacitor and resistors coupled to transistors 549, 552 in a matter as will be appreciated by those having ordinary skill in the art.

In operation of the control circuit 550, in the presence of an appropriate signal on line 710, such as a logic "0" level signal or some other negative signal indicating welding has not been detected, for example, the transistor 552 is not conductive, and the transistor 549 is not conductive. Therefore, high voltage from line 545 will not be delivered to the input power line 506. However, when a logic high signal is provided on line 710 indicating a call for high voltage to be supplied to the input power line 506 to cause the shutter 10 to assume the dark state (being powered to a high voltage applied across the terminals 509, 510 of the power output circuit 505), the transistor 552 becomes conductive, and the transistor 549 promptly becomes substantially fully conductive. Therefore, the full voltage on line 545 is delivered the input power line 506. Diode 539 blocks coupling of the relatively high voltage on the input power line 30 from reaching the low voltage drive circuit 516.

The capacitor 553 helps to pull down (in voltage or potential) the gate of the field effect transistor 549 immediately when the transistor 552 turns on. This overcomes capacitance in the gate of the transistor 549 and helps to speed up the turn on to conduction of the transistor. Moreover, after the capacitor 553 has helped to turn on the transistor 549, such transistor will be maintained conductive by current from the resistor divider circuit (768) included in circuit 550 while the transistor 552 remains conductive. Ordinarily the current required to maintain the field effect transistor 549 conductive is less than that required initially to turn it on; by reducing the base signal using the resistors some power is saved in the power supply circuit 500.

The high voltage power supply circuit 518 is operative initially to provide via the high voltage drive circuit 515 a high voltage to the variable retarder in the shutter 10 to expedite transition to dark state. Thereafter, a reduced voltage that is adequate to maintain the dark state is provided to the shutter by the circuits 518 and 516. Such dark state maintaining voltage, though, ordinarily would be greater than the low voltage provided at the output of the low voltage drive circuit 516, which is used to maintain the clear state for the shutter 10.

Dark State Voltage Adjustment circuit 522, and detachable/remote fine tuning adjustment 523

The dark state adjusting circuit 522 includes the resistors 554, 555, 556, the resistor 555 being an adjustable potentiometer. By adjusting the potentiometer 555, and, thus, the voltage output of the resistor voltage divider circuit formed by the resistors 554, 555, 556, the value of the voltage on line 557 can be adjusted. Accordingly, such adjustment of the potentiometer 555 effectively adjusts the magnitude of the regulated high voltage on the high voltage line 545 for maintaining the dark state of the shutter 10 after it initially is driven to dark condition. This provides a means for controlling how much incident light is blocked by the shutter 10 when in the dark state. Because the resistance of the potentiometer 555 is adjustable over a continuous range, the shutter 10 can be adjusted according to an infinite number of settings between two extremes. This is a significant advantage over conventional shutters which offer only a few distinct settings of dark state. The resistors 554, 556 are used to limit the voltage range achievable on line 557 in a matter that is apparent to those having normal knowledge of the art.

Figure 4:
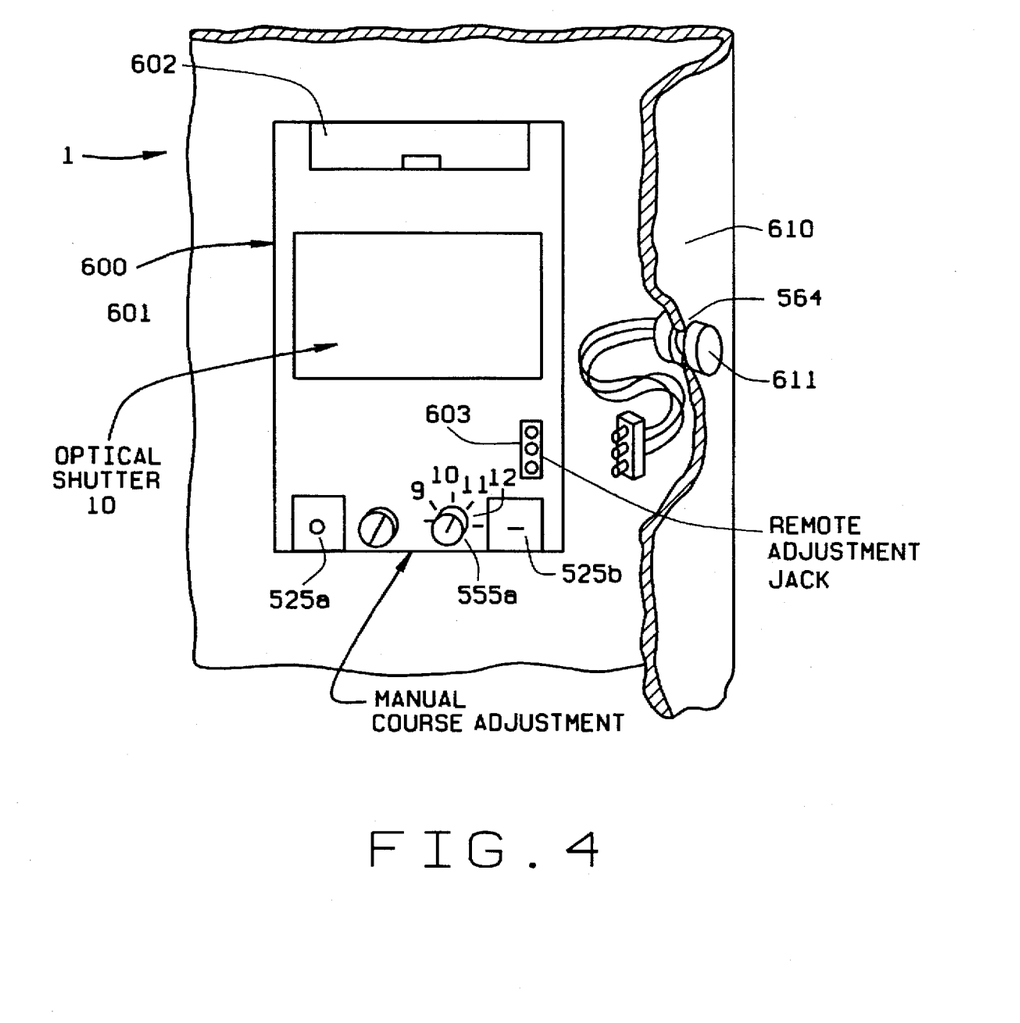
FIG. 4 is a schematic illustration of a detachable remote fine tuning circuit for use in a welding helmet employing the shutter and driving circuits of the invention.

The fine tuning circuit 523 can be used preferably while a person is using the shutter 10, for example, while the welding helmet 1 is being worn. The fine tuning circuit 523 allows small adjustments to be made to the shade (darkness) of the shutter 10 over a limited range to the desire of the welder. Since preferably large changes in shade cannot be made by the fine tuning circuit, the possibility of the welder making the shutter too light (clear) while welding and, thus, possibly allowing too much light to reach the eyes, is avoided. A larger range of adjustment of shade can be made by adjusting the dark state adjust potentiometer 555. However, that adjustment preferably is not easily accessible, and especially is not directly accessible while the welding helmet is worn. Connections of the fine tuning circuit and mounting of it in the welding helmet with respect to the welding shutter 10 are shown in FIG. 4, which is described further below. Although the fine tuning circuit 523 is illustrated for operation in the power supply circuit 500, it also may be used in a similar manner in the power supply circuit 14 or in other appropriate power supply circuits.

The value of the voltage on line 557, and thus the output voltage to the shutter 10, can be further adjusted by using the fine tuning circuit 523 which preferably is detachable and/or remotely located as described below. The fine tuning circuit 523 is made up of resistor 563 and potentiometer 564. If the fine tuning is not being used (not attached) it has no influence on the power supply circuit 500 operation. When the remote fine tuning circuit is attached via a connector 603, the adjustment of the potentiometer 564 will yield a relatively small change of the voltage on line 557. The magnitude of the maximum change due to potentiometer 564 adjustment would typically be on the order of about 20% of the adjustment range achieved when using potentiometer 555. The potentiometer 564 would typically be located in a position on the welding helmet remote from the power supply circuit 500 that would allow the welder to easily fine tune the power supply circuit 500 while welding to optimize comfort and productivity.

The magnitude of the voltage at line 545 from the high voltage power supply 518 is determined in the following manner: In the clear state, when the high voltage control circuit is not activated, the high voltage power supply circuit 518 produces the voltage on line 545 by comparing the feedback voltage on line 548 with the regulated reference voltage on line 736, the comparison being made by the comparator 760 in the integrated circuit 527 as described above. In the dark state, the integrated circuit 527 compares the feedback voltage on line 548 with the voltage produced by the dark state voltage adjustment circuit at line 557. If the feedback voltage is less than the voltage on line 557, the power supply is activated by a signal on line 547 as described above until such time as the feedback voltage has attained the corresponding level. The output of the high voltage output circuit 518 during the clear state is preferably about 40 volts. The output of the circuit during the dark state is preferably in the 10 to 18 volt range. It will be appreciated that the high voltage and clear state voltage may be other than those described herein, e.g., depending on circuit component values, shutter requirements, etc.

During the transition from the clear state to the dark state, i.e. when the sensor circuit 519 detects welding light, the voltage produced by the high voltage power supply circuit 518 is reduced from about 40 volts to the required voltage to maintain the shutter 10 in the dark state. The storage capacity of the capacitor 544 prevents immediate change between the very high, say 40 volts, and lower, say 15 volts, output from the high voltage power supply circuit 518.

The high voltage 40 volt signal expedites switching of the shutter 10 to the dark state. The lower voltage 15 volt signal is adequate to maintain the dark state thereafter. The voltage reduction reduces power draw on the battery 502.

Sensor Circuit 519

The sensor circuit 519 includes a pair of photosensitive or photodetector circuits which provide an input signal to integrated circuit 527 that detect incidence of welding light on the photodetector. These input signals are used to determine the state of the outputs to the liquid crystal shutter 10. The details of operation of the sensor circuit 519 are described in commonly assigned, copending U.S. patent application Ser. No. 07/814,372, filed Dec. 26, 1991, the entire disclosure of which is incorporated herein by reference. Briefly, each detector circuit 200' includes a transistor 17 for sensing the incident light. A sensitivity feedback circuit 780 controls the bias voltage provided to the phototransistor 17 and enables the shutter 10 to have a wide range of operation spanning dark and bright ambient light conditions. A threshold feedback circuit 782 controls the level of the threshold voltage provided to a comparator 786. The comparator 786 compares the output of the phototransistor 17 to the threshold voltage. When the output of the phototransistor 17 exceeds that of the threshold voltage, thereby indicating that welding has occurred, the output of the comparator 786 goes low causing the output of NAND gate 788 to go high.

The output of the NAND gate 788 is coupled to a falling edge delay circuit 790 which includes a field effect transistor 792 and the inverter 709. When welding is detected the output of the falling edge delay circuit 790 goes high substantially immediately whereby the signal on line 710 goes high indicating the occurrence of welding. When welding terminates, the output of the comparator 786 goes low. The falling edge delay circuit 790 delays the transition on line 710 to a logic low level for a predetermined time sufficient to ensure that welding has indeed terminated prior to the shutter 10 being driven back to a clear state. This feature is particularly important when engaging in pulse-type welding as will be appreciated.

Variable Delay Circuit 521

The duration of the delay provided by the falling edge delay circuit 790 is a function of the values of capacitor 558 and resistors 559, 560. The capacitor 558 is coupled between the source of transistor 792, the input of the inverter 709, and ground. Resistors 559 and 560 are connected between line 528 and the input of the inverter to form an RC network having a time constant related to the desired delay.

Capacitor 558 and resistors 559, 560 provide a time delay of, for example, one fourth second (or some other time), to prevent constant detection and undetection of welding in the event that the pulsed type of welding light occurs or the welder briefly turns is or her head from viewing the welding light or otherwise briefly loses a light path connection between the welding light and the photodetector in the sensor circuit 519. By adjusting variable resistor 560, the delay can be optimized for a particular welding style, e.g., either longer or shorter. An exemplary delay range would be from 0.1 seconds to 0.75 seconds.

Frequency Varying Circuit 520

The frequency varying circuit 520 includes capacitor 561 and a voltage controlled oscillator (VCO) 800 contained within the integrated circuit 527.

When welding is not detected, the frequency varying circuit 520 produces an output signal on line 802 at a frequency based on the external capacitor 561. This value would typically be on the order of 50 Hz., although the actual frequency may be larger or smaller. The VCO 800 includes a "mode" input which effectively fixes the frequency of the output signal on line 802 to the value based on the capacitor 561 when the level of the signal on line 710 coupled to the mode input is low. Preferably the frequency is adequate to minimize power required for driving the shutter 10 while avoiding flicker. The output on line 802 serves as the clock input to flip-flop 804 having outputs Q and Q-bar which are connected to lines 507, 508 from the integrated circuit 527 to control operation of the power supply circuit 505 and, thus, shutter 10.

When the sensor circuit 519 detects welding, the power supply circuit 500 is in the dark state and the signal on line 710 is high. This causes the VCO 800 to produce an output signal on line 802 having a frequency which is inversely proportional to the voltage input provided to the VCO from line 548 (and hence the scaled output voltage to shutter 10). That is, as the voltage to the shutter 10 increases, the frequency decreases. As a result, the power required to drive the shutter is reduced. This inverse proportion preferably is a continuous function, but it also may be a step function. Also, since the shutter then is operating in the dark state, any problem due to flicker is avoided.

SUMMARY OF OPERATION OF THE POWER SUPPLY CIRCUIT 500 WITH THE SHUTTER 10

When the momentary contact (start) power switch 525a is closed, the time out circuit 512 is reset to count for 25–30 minutes, and battery voltage is provided to line 528 until the time out circuit shuts down the power supply circuit 500. If the voltage of battery 502 is below a prescribed minimum, the light emitting diode 530 will flash or blink. Alternatively, or in addition, a speaker 810 connected in place of or in parallel with the light emitting diode 530 will beep and provide an audible indication of low battery power. In still another embodiment, the light emitting diode 530 may in fact be a series of diodes which blink on and off.

Upon closing the switch 525a, the start/initialization circuit 524 will cause the high voltage power supply circuit 518 to rapidly charge to its maximum high voltage level of, say, 40 volts ready to drive the shutter 10 to the dark state. The closed switch 525 will turn on transistor 552 to conduction, which, in turn, turns on the transistor 549; and the latter then supplies the high voltage from line 545 of the output of the high voltage power supply circuit 518 to the shutter 10 to set up the directors in or to assure they are set up in a desired alignment for operation of the variable retarder 11. After the start/initialization circuit 524 counts for approximately 2 seconds, if welding has not yet occurred, then the low voltage drive circuit 516 provides a voltage through the diode 539 to maintain the shutter in the clear state. However, when welding subsequently is detected (or if welding were detected while the start/initialization circuit still were in its initialization mode), a logic 1 signal is produced on line 710 to turn on the high voltage drive circuit 515, which then delivers the initial high voltage from line 545 to the power output circuit 505 to expedite turn on of the shutter to the dark condition. Also, thereafter while welding continues to be detected, high voltage power supply circuit 518 will reduce the output voltage to a level determined by the dark state adjustment circuit. The reduced dark state voltage is of a level to maintain the shutter in the dark state. The frequency of the shutter drive signal at terminals 509, 510, will be a function of the frequency varying circuit 520, which produces a higher frequency signal when clear state is required and a lower (but non-zero to avoid polarizing the liquid crystal and/or other detrimental affects) frequency signal when dark state is required. The dark state voltage, and thus the transmission of the shutter 10 can be adjusted by using the high voltage adjustment circuit 522, and the remote fine tuning circuit 523. The delay that the circuit takes to go from the dark state to the clear state can be adjusted by using potentiometer 560 in the variable delay circuit 521 to optimize the delay for different types of welding.

FINE TUNE TUNING CIRCUIT 523 MOUNTING AND CONNECTION

Briefly referring to FIG. 4, the welding helmet 1 is shown in a schematic, fragmentary view. The shutter 10 is seen from within the welding helmet 1 as part of a shutter module 600, which includes a case 601 containing the various optical parts of the shutter 10, including the variable retarder 11, the battery 21 in a battery compartment 602, and the other parts of the power supply circuit 14 or 500. The photodetectors are not seen in FIG. 4, for they are on the back side of the paper in which FIG. 4 is drawn, but it will be appreciated that such photodetectors and associated circuitry also are contained in and/or mounted on the shutter module 600. The start and stop switches 525a, 525b and an adjustable knob 555a of the dark state adjustment potentiometer 555 (FIG. 3) are seen in FIG. 4.

A connector 603 mounted in the case 601 provides an electrical connection to the fine tuning circuit 523 and to the lines 605, 606, 607 (FIG. 3) thereof in the power supply circuit 500. The potentiometer 564 of the fine tuning circuit 523 is mounted in an opening 608 in a wall 610 of the welding helmet 1 to permit adjustment of the potentiometer 564 from outside of the helmet, e.g., by the welder turning a knob 611. An electrical cable connector 612 connects the potentiometer 564 to the connector 603. Preferably the cable connector 612 can be selectively used, depending on whether or not the welding helmet 1 is to have the fine tuning adjustment capability. If it is not used, then the potentiometer 564 is not connected in the power supply circuit 500, and there will be no fine tuning capability therefor. The connector 603 may have sensors to detect the presence of the cable connector 612 connected or not thereto and depending thereon may set up appropriate connections in the fine tuning adjust circuit 523 within the power supply circuit 500 so that the omission of the potentiometer therefrom does not affect proper operation of the power supply circuit.

Preferably the mounting mechanism 613 for mounting the potentiometer in the opening 608 is universal; and preferably the opening 608 can be formed at virtually any convenient location in the wall 610 of the welding helmet 1. Therefore, the user of the welding helmet may decide the most convenient location in the welding helmet for her or him to mount the potentiometer 564, can drill an opening 608 there, can mount the potentiometer in the opening, and can connect the cable connector 612 between the potentiometer and the connector 603. Alternatively, the potentiometer 564 can be mounted in the welding helmet 1 during the initial manufacturing thereof.

STATEMENT OF INDUSTRIAL APPLICATION

From the foregoing it will be appreciated that the power supply circuit 14 and the alternate power supply circuit 500 are useful in energizing a variable retarder 11 in a welding lens shutter 10 used, for example, in a welding helmet or other eye protecting or device protecting apparatus.

We claim:

1. A portable power supply for a protective optical lens system that has at least relatively greater and lesser light transmission characteristics, comprising a regulated power supply for supplying substantially regulated power for driving such lens system from an unregulated power source, said regulated power supply comprising a regulated voltage reference, a DC to DC oscillator, a voltage power input, and inductor and capacitor circuit with diode isolation to develop and to store in said capacitor a voltage of a magnitude greater than the voltage of said voltage power input, a switch for switching a connection between said inductor and capacitor, said oscillator being coupled to operate said switch to open and close state to accumulate charge and voltage in said capacitor, and a comparator circuit for comparing the voltage of said capacitor with said regulated voltage reference to control operation of said oscillator to develop a voltage in said capacitor in proportional relation to a comparison between said regulated voltage reference and the voltage in said capacitor, output circuit means for coupling power from said regulated power supply to such lens system to cause such lens system to achieve greater and lesser light transmission characteristics.

2. The power supply of claim 1, said output circuit means comprising a level control means to adjust regulated power output level to achieve greater or lesser light transmission characteristics.

3. The power supply of claim 1, further comprising dark state adjust means for adjusting the darkness of the optical lens system in the lesser light transmission state over a prescribed range.

4. The power supply of claim 3, further comprising variable fine tuning adjustment means for further adjusting the darkness of the optical lens system in the lesser light transmission state over a range that is a percentage less than 100% of the range of said dark state adjust means.

5. The power supply of claim 1, further comprising an unregulated power supply comprising a depletable power source.

6. The power supply of claim 5, said unregulated power supply comprising a battery.

7. The power supply of claim 5, said unregulated power supply comprising a capacitor.

8. The power supply of claim 1, further comprising an unregulated power supply comprising a solar cell.

9. A portable power supply for a protective optical lens system that has at least relatively greater and lesser light transmission characteristics, comprising input means for receiving an electrical input from a depletable power source, circuit means coupled to said input means for converting such electrical input for use to operate such lens system, monitor means for monitoring the power level of the electrical input received from such power source, signal means coupled with respect to said monitor means for signaling that such power level has dropped below a prescribed level, said monitor means comprising a comparator circuit for comparing the voltage of such electrical input with a regulated voltage, and said signal means being coupled to said comparator circuit to be energized thereby when a voltage proportionally representative of such electrical input drops below the voltage established by such regulated voltage.

10. The power supply of claim 9, said depletable power source comprises a battery.

11. The power supply of claim 9, said depletable power source comprises a capacitor.

12. The power supply of claim 9, said signal means comprising a light emitting diode.

13. The power supply of claim 9, said signal means comprising a series of light emitting diodes.

14. The power supply of claim 9, said signal means comprising a multicolor light emitting diode.

15. The power supply of claim 9, said signal means comprising a light.

16. The power supply of claim 9, said signal means comprising an audible indicator.

17. The power supply of claim 9, said monitor means comprising a comparator circuit for comparing the voltage of such electrical input with a regulated voltage, and said signal means being coupled to said comparator circuit to be energized thereby when a voltage proportionally representative of such electrical input drops below the voltage established by such regulated voltage.

18. A portable power supply for a protective optical lens system that has at least relatively greater and lesser light transmission characteristics, comprising a regulated power supply for supplying substantially regulated power for driving such lens system in response to a power input from a power source, circuit means coupled to said input means for converting such electrical input for use to operate such lens system, output circuit means for coupling power from said regulated power supply to such lens system to cause such lens system to achieve greater and lesser light transmission characteristics, monitor means for monitoring the power level of the electrical input received from such power source, signal means coupled with respect to said monitor means for signaling that such power level has dropped below a prescribed level.

19. Protective eye gear for welding, comprising a variable shutter to control the amount of light transmitted to the eyes, the shutter being operable between relatively clear and relatively dark states, a power supply circuit for the shutter, mounting means for mounting the shutter, dark state adjusting circuit for determining the light transmission and blocking characteristics of the shutter when in the reduced transmission state, an adjustment device for adjusting said dark state adjusting circuit, said adjusting device being relatively inaccessible to a user wearing the protective eye gear, and variable fine tune adjusting means accessible while the eye gear is worn by a person for limited adjustment of the dark state over a range that is significantly smaller than the full range of the dark state adjusting circuit thereby to avoid accidental adjustment to the relatively clear state while welding is occurring and means for selectively connecting said variable fine tune adjusting means to the power supply.

20. The eye gear of claim 19, said eye gear comprising a welding helmet having a wall, and wherein at least part of said variable fine tune adjusting means is mounted in said wall.

21. Protective eye gear, comprising:

a variable shutter to control the amount of light transmitted to the eyes, the shutter being operable between relatively clear and relatively dark states;

a power supply circuit for the variable shutter;

first adjusting means for adjusting the dark state; and second adjusting means for adjusting the dark state.

22. The eye gear of claim 21, wherein the first and second adjusting means provide for adjustment of the dark state over a first and second adjustment range, respectively.

23. The eye gear of claim 22, wherein the second adjustment range is a fraction of the first adjustment range.

24. The eye gear of claim 21, further comprising a helmet having a wall, and wherein at least part of the second adjusting means is mounted to the wall.

25. The eye gear of claim 21, further comprising means for selectively connecting the second adjusting means to the power supply.

26. Protective eye gear, comprising:

a variable shutter to control the amount of light transmitted to the eyes, the shutter being operable between relatively clear and relatively dark states; and means for selectively adjusting a time which it takes for the shutter to transition from the relatively dark state to the relatively clear state.

27. The eye gear of claim 26, said means for adjusting comprising a potentiometer.

28. A power supply for a protective optical shutter that is operable between relatively clear and relatively dark states, comprising:

power supply means for providing a driving signal to drive the optical shutter; and frequency varying means for adjusting the frequency of said driving signal as a function of whether the optical shutter is to be driven in the relatively clear state or the relatively dark state, and wherein the driving signal has a relatively low frequency when driving the optical shutter in the relatively dark state and a relatively high frequency when driving the optical shutter in the relatively clear state.

29. The power supply of claim 28, wherein the driving signal has a relatively large magnitude to drive the optical shutter in the relatively dark state and a relatively small magnitude to drive the optical shutter in the relatively clear state.

30. An energization circuit for a liquid crystal light shutter device, comprising output means for supplying an output to the liquid crystal device for causing such device to produce at least two different optical responses, one output comprising a relatively low voltage level to cause relatively high light transmission optical response and a second output comprising a relatively high voltage level to cause a relatively low light transmission optical response.

driving means for driving said output means at one level to produce one optical response and at a second level to produce the second optical response, said driving means including frequency means for changing the frequency at which said output means is driven whereby at such one relatively low voltage level the frequency is relatively higher than the frequency at such second level.

31. The eye gear of claim 19, wherein the magnitude of the maximum change due to the fine tune adjustment is on the order of about 20% of the adjustment range achieved when using said adjusting device.

* * * * *